United States Patent [19]

Riebel

[11] Patent Number: 4,968,796
[45] Date of Patent: Nov. 6, 1990

[54] PREPARATION OF SULPHONYLISOTHIOUREAS

[75] Inventor: Hans-Jochem Riebel, Wuppertal, Fed. Rep. of Germany

[73] Assignee: Bayer Aktiengesellschaft, Leverkusen, Fed. Rep. of Germany

[21] Appl. No.: 395,228

[22] Filed: Aug. 17, 1989

[30] Foreign Application Priority Data

Aug. 31, 1988 [DE] Fed. Rep. of Germany ....... 3829469

[51] Int. Cl.$^5$ ............... C07D 251/70; C07D 251/50; C07D 251/52; C07D 251/44; C07D 251/46; C07D 239/47; C07D 239/42; C07D 239/48; C07D 239/50; C07D 213/72; C07D 213/61; C07D 213/62

[52] U.S. Cl. .................... 544/211; 544/197; 544/198; 544/205; 544/206; 544/207; 544/196; 544/208; 544/209; 544/210; 544/212; 544/213; 544/182; 544/310; 544/311; 544/312; 544/317; 544/320; 544/321; 544/323; 544/324; 544/327; 544/331; 544/332; 544/295; 544/296; 544/241; 544/224; 544/239; 544/240; 544/238; 544/199; 544/179; 546/261; 546/307; 546/143; 546/264; 546/310; 546/262; 546/312; 546/263; 546/315; 546/280; 546/318; 546/284; 546/328; 546/279; 546/326; 546/270; 546/322; 546/269; 546/334; 546/286; 546/288; 546/289; 546/298; 546/300

[58] Field of Search ............... 544/196, 197, 198, 207, 544/210, 213, 311, 320, 324, 332, 295, 224, 238, 90, 205, 206, 208, 209, 211, 212, 182, 310, 312, 317, 321, 323, 327, 331, 296, 241, 239, 240, 199, 179; 546/261, 264, 312, 280, 328, 270, 334, 289, 307, 143, 310, 262–263, 315, 318, 284, 279, 326, 322, 269, 286, 288, 298, 300

[56] References Cited

FOREIGN PATENT DOCUMENTS 0005986 12/1979 European Pat. Off. .

Primary Examiner—John M. Ford
Attorney, Agent, or Firm—Sprung Horn Kramer & Woods

[57] ABSTRACT

Disclosed is a process for the preparation of a sulphonylisothiourea of the formula

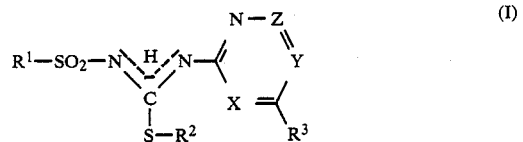

(I)

wherein $R^1$, $R^2$, $R^3$, X, Y, and Z are as defined herein, which comprises reacting a sulphonic acid amide of the formula

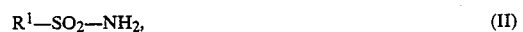

(II)

or a metal salt thereof, with an N-heteroaryl-iminodithiocarbonic acid S,S-diester of the formula

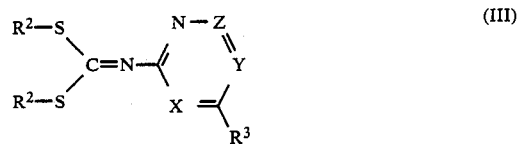

(III)

at a temperature between about 20° C. and 200° C. Intermediates and a process for their preparation are also disclosed.

6 Claims, No Drawings

PREPARATION OF SULPHONYLISOTHIOUREAS

The invention relates to a new process for the preparation of known sulphonylisothioureas and new intermediate products for this process.

It is known that sulphonylisothioureas are obtained when sulphonylthioureas are converted into salts and these are reacted with alkylating agents (compare EP-A No. 5,986).

Several reaction steps are required for the preparation of the sulphonylthioureas required as starting substances in this process: corresponding sulphonic acid amides are first reacted with carbon disulphide and potassium hydroxide to give dipotassium salts of sulphonyliminodithiocarbonic acids; reaction thereof with phosgene leads to sulphonylisothiocyanates, and corresponding sulphonylthioureas are obtained from the latter with amino compounds. This synthesis route to give sulphonylisothioureas requires a high expenditure on apparatus in some stages and in addition does not always lead to satisfactory results in respect of the yield and quality of the products.

It has now been found that sulphonylisothioureas of the general formula (I)

$$R^1-SO_2-N\underset{\underset{S-R^2}{|}}{\overset{H}{\underset{C}{|}}}N=\underset{X}{\overset{N-Z}{\diagdown}}\overset{Y}{\underset{R^3}{=}}\quad(I)$$

in which
R[1] represents an optionally substituted radical from the series comprising alkyl, aralkyl, aryl and heteroaryl,
R[2] represents in each case optionally substituted alkyl or aralkyl,
R[3] represents hydrogen, halogen, hydroxyl, amino or an optionally substituted radical from the series comprising alkyl, alkoxy, alkylthio, alkylamino and dialkylamino,
X represents nitrogen or a CH grouping,
Y represents nitrogen or a CR[4] grouping, wherein
R[4] represents hydrogen, halogen, cyano, alkyl, formyl, alkylcarbonyl or alkoxycarbonyl, and
Z represents nitrogen or a CR grouping, wherein
R[5] represents hydrogen, halogen, hydroxyl, amino or an optionally substituted radical from the series comprising alkyl, alkoxy, alkylthio, alkylamino and dialkylamino, are obtained in a simple manner in high yields by a process in which sulphonic acid amides of the general formula (II)

$$R^1-SO_2-NH_2 \quad (II)$$

in which
R[1] has the abovementioned meaning,
—or metal salts of compounds of the formula (II)—are reacted with N-heteroaryl-iminodithiocarbonic acid S,S-diesters of the general formula (III)

$$\underset{R^2-S}{\overset{R^2-S}{\diagdown}}C=N-\underset{X}{\overset{N-Z}{\diagdown}}\overset{Y}{\underset{R^3}{=}}\quad(III)$$

in which
R[2], R[3], X, Y and Z have the abovementioned meanings, if appropriate in the presence of an acid acceptor and in the presence of a diluent at temperatures between 20° C. and 200° C.

Surprisingly, with the aid of the process according to the invention, it is possible to prepare the compounds of the formula (I) in high yields in a relatively simple manner.

If, for example, 2-fluoro-benzenesulphonamide and S,S-dimethyl N-(4,6-dimethoxy-pyrimidin-2-yl)-iminodithiocarbonate are used as starting substances, the course of the reaction can be outlined by the following equation:

The sulphonic acid amides used as starting substances are defined generally by the formula (II). Preferably, in formula (II),
R[1] represents the radical wherein
R[6] represents hydrogen, halogen, cyano, nitro, $C_1-C_4$-alkyl (which is optionally substituted by halogen, cyano, $C_1-C_4$-alkoxy or $C_1-C_4$-alkoxycarbonyl), $C_1-C_4$-alkoxy (which is optionally substituted by halogen, cyano, $C_1-C_4$-alkoxy or $C_1-C_4$-alkoxy-carbonyl) or $C_1-C_4$-alkylthio, $C_1-C_4$-alkylsulphinyl or $C_1-C_4$-alkylsulphonyl (which are optionally substituted by halogen, cyano, $C_1-C_4$-alkoxy or $C_1-C_4$-alkoxy-carbonyl), or represents di-($C_1-C_4$-alkyl)-aminosulphonyl, N-($C_1-C_4$-alkoxy)-N-$C_1-C_4$-alkyl-aminosulphonyl, phenyl, phenoxy, $C_1$–$C_4$-alkoxy-carbonyl or di-($C_1$–$C_4$-alkylamino)-carbonyl and
$R^7$ represents hydrogen or halogen,
or, preferably,
$R^1$ represents the radical

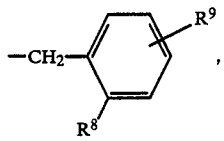

wherein
$R^8$ represents hydrogen, halogen, cyano, nitro, $C_1$–$C_4$-alkyl (which is optionally substituted by halogen, cyano, $C_1$–$C_4$-alkoxy or $C_1$–$C_4$-alkoxy-carbonyl), $C_1$–$C_4$-alkoxy (which is optionally substituted by halogen, cyano, $C_1$–$C_4$-alkoxy or $C_1$–$C_4$-alkoxy-carbonyl) or $C_1$–$C_4$-alkylthio, $C_1$–$C_4$-alkylsulphinyl or $C_1$–$C_4$-alkylsulphonyl (which are optionally substituted by halogen, cyano, $C_1$–$C_4$-alkoxy or $C_1$–$C_4$-alkoxy-carbonyl), or represents di-($C_1$–$C_4$-alkyl)-aminosulphonyl or $C_1$–$C_4$-alkoxy-carbonyl and
$R^9$ represents hydrogen or halogen,
or, preferably,
$R^1$ represents the radical

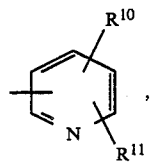

wherein
$R^{10}$ represents hydrogen, halogen, cyano, nitro, $C_1$–$C_4$-alkyl (which is optionally substituted by halogen), $C_2$–$C_4$-alkenyl (which is optionally substituted by halogen), $C_1$–$C_4$-alkoxy (which is optionally substituted by halogen), $C_1$–$C_4$-alkylthio, $C_1$–$C_4$-alkylsulphinyl or $C_1$–$C_4$-alkylsulphonyl (which are optionally substituted by halogen), di-($C_1$–$C_4$-alkyl)-aminosulphonyl, $C_1$–$C_4$-alkoxycarbonyl, di-($C_1$–$C_4$-alkyl)-aminocarbonyl or dioxolanyl and
$R^{11}$ represents hydrogen or halogen,
or, preferably,
$R^1$ represents the radical

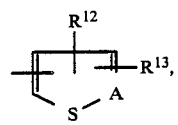

wherein
A represents nitrogen or a CH grouping,
$R^{12}$ represents hydrogen, halogen, cyano, nitro, $C_1$–$C_4$-alkyl (which is optionally substituted by halogen, $C_1$–$C_4$-alkoxy or $C_1$–$C_4$-halogenoalkoxy), $C_1$–$C_4$-alkoxy (which is optionally substituted by halogen or $C_1$–$C_4$-alkoxy), $C_1$–$C_4$-alkylthio, $C_1$–$C_4$-alkylsulphinyl or $C_1$–$C_4$-alkylsulphonyl (which are optionally substituted by halogen), di-($C_1$–$C_4$-alkyl)-aminosulphonyl or $C_1$–$C_4$-alkoxycarbonyl and
$R^{13}$ represents hydrogen or halogen,
or, preferably,
$R^1$ represents the radical

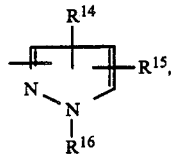

wherein
$R^{14}$ represents hydrogen, halogen, cyano, nitro, $C_1$–$C_4$-alkyl (which is optionally substituted by halogen), $C_1$–$C_4$-alkoxy (which is optionally substituted by halogen), dioxolanyl or $C_1$–$C_4$-alkoxy-carbonyl,
$R^{15}$ represents hydrogen or halogen and
$R^{16}$ represents hydrogen, $C_1$–$C_4$-alkyl, phenyl or (iso)quinolinyl,
or, preferably,
$R^1$ represents the radical

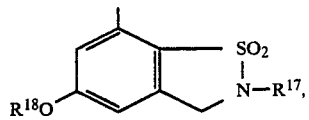

wherein
$R^{17}$ and $R^{18}$ represent $C_1$–$C_4$-alkyl,
or, preferably,
$R^1$ represents the radical

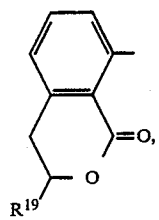

wherein
$R^{19}$ represents hydrogen or methyl.
Starting substances which are particularly preferred are the compounds of the formula (II) in which
$R^1$ represents the radical

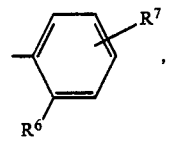

wherein
$R^6$ represents fluorine, chlorine, bromine, methyl, trifluoromethyl, methoxy, difluoromethoxy, trifluoromethoxy, methylthio, methylsulphonyl, dimethylaminosulphonyl, N-methoxy-N-methylaminosulphonyl, phenyl, methoxycarbonyl or ethoxycarbonyl and
$R^7$ represents hydrogen, fluorine or chlorine.

Examples which may be mentioned of the starting substances of the formula (II) are: 2-fluoro-, 2-chloro-, 2-bromo-, 2,5-dichloro-, 2,6-dichloro-, 2-methyl-, 2-trifluoromethyl-, 2-methoxy-, 2-difluoromethoxy-, 2-trifluoromethoxy-, 2-methylthio-, 2-methylsulphonyl-, 2-dimethylaminosulphonyl-, 2-(N-methoxy-N-methylamino)-sulphonyl, 2-phenyl-, 2-methoxycarbonyl- and 2-ethoxycarbonyl-benzenesulphonamide.

The starting substances of the formula (II) are known and/or can be prepared by processes which are known per se (compare U.S. Pat. No. 4,371,391; J. Org. Chem. 27 (1962), 1703-1709; U.S. Pat. Nos. 4,310,346; 4,452,628; EP-A Nos. 44,808; 87,780; U.S. Pat. No. 4,732,711 and EP-A No. 271,780).

Formula (III) provides a general definition of the N-heteroaryl-iminodithiocarbonic acid S,S-diesters furthermore to be employed as starting substances. Preferably, in formula (III), $R^2$ represents $C_1$–$C_6$-alkyl (which is optionally substituted by fluorine, chlorine, cyano, $C_1$–$C_2$-alkoxy, carboxyl, $C_1$–$C_2$-alkoxy-carbonyl, aminocarbonyl, $C_1$–$C_2$-alkylaminocarbonyl or di-($C_1$–$C_2$-alkyl)-amino-carbonyl, or represents benzyl or phenethyl (which are optionally substituted in the phenyl part by fluorine, chlorine, $C_1$–$C_2$-alkyl, $C_1$–$C_2$-halogenoalkyl, $C_1$–$C_2$-alkoxy, $C_1$–$C_2$-halogenoalkoxy or $C_1$–$C_2$-alkoxycarbonyl), $R^3$ represents hydrogen, fluorine, chlorine, bromine, $C_1$–$C_4$-alkyl, $C_1$–$C_4$-halogenoalkyl, $C_1$–$C_2$-alkoxy-$C_1$–$C_2$-alkyl, $C_1$–$C_4$-alkoxy, $C_1$–$C_4$-halogenoalkoxy, $C_1$–$C_4$-alkylthio, $C_1$–$C_4$-halogenoalkylthio, amino, $C_1$–$C_4$-alkylamino, dimethylamino or diethylamino, X represents nitrogen or a CH grouping, Y represents nitrogen or a $CR^4$ grouping, wherein
  $R^4$ represents hydrogen, fluorine, chlorine, bromine, cyano, methyl, formyl, acetyl, methoxycarbonyl or ethoxycarbonyl and Z represents nitrogen or a CR grouping, wherein
  $R^5$ represents hydrogen, fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-alkylamino, dimethylaminoor diethylamino.

Particularly preferred starting substances are the compounds of the formula (III) in which $R^2$ represents methyl, ethyl, carboxymethyl, methoxycarbonylmethyl, ethoxycarbonylmethyl or benzyl, $R^3$ represents hydrogen, fluorine, chlorine, bromine, methyl, ethyl, trifluoromethyl, methoxy, ethoxy, difluoromethoxy, methylthio, ethylthio, amino, methylamino, ethylamino, dimethylamino or diethylamino, X represents nitrogen or a CH grouping, Y represents nitrogen or a $CR^4$ grouping, wherein
  $R^4$ represents hydrogen, fluorine, chlorine or methyl, and Z represents nitrogen or a $CR^1$ grouping, wherein
  $R^5$ represents hydrogen, fluorine, chlorine, bromine, methyl, ethyl, trifluoromethyl, methoxy, ethoxy, propoxy, isopropoxy, difluoromethoxy, methylthio, ethylthio, methylamino, ethylamino, dimethylamino or diethylamino.

Examples of the starting substances of the formula (III) are listed in the following Table 1.

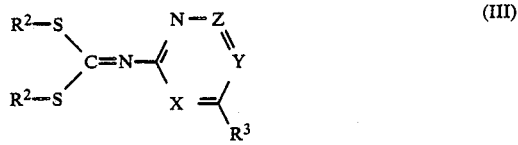

TABLE 1

Examples of the starting substances of the formula (III)

| $R^2$ | $R^3$ | X | Y | Z |
|---|---|---|---|---|
| $CH_3$ | $CH_3$ | N | CH | C—$CH_3$ |
| $CH_3$ | $CH_3$ | N | CH | C—$OCH_3$ |
| $CH_3$ | $OCH_3$ | N | CH | C—$OCH_3$ |
| $CH_3$ | $OCH_3$ | N | CH | C—Cl |
| $CH_3$ | $CH_3$ | N | CH | C—$CH_3$ |
| $CH_3$ | $CF_3$ | N | CH | C—$OCH_3$ |
| $CH_3$ | $OCH_3$ | N | CH | C—$OCHF_2$ |
| $CH_3$ | $CH_3$ | N | CH | C—$OCHF_2$ |
| $CH_3$ | $CH_3$ | N | N | C—$CH_3$ |
| $CH_3$ | $CH_3$ | N | N | C—$OCH_3$ |
| $CH_3$ | $OCH_3$ | N | N | C—$OCH_3$ |
| $CH_3$ | $C_2H_5$ | N | CH | C—$OCH_3$ |
| $CH_3$ | $CH_3$ | N | N | C—$OC_2H_5$ |
| $CH_3$ | $C_2H_5$ | N | N | C—$OCH_3$ |
| $CH_3$ | $CH_3$ | N | N | C—Cl |
| $CH_3$ | $CH_3$ | CH | N | C—$CH_3$ |
| $CH_3$ | $OCHF_2$ | N | CH | C—$OCHF_2$ |
| $CH_3$ | $OCH_3$ | CH | N | C—$OCH_3$ |
| $CH_3$ | $CH_3$ | N | CH | C—$SCH_3$ |
| $CH_3$ | $CH_3$ | N | CH | C—$N(CH_3)_2$ |
| $CH_3$ | $OCH_3$ | N | CH | C—$SCH_3$ |
| $CH_3$ | $OCH_3$ | N | N | C—$NHC_2H_5$ |
| $CH_3$ | $OC_2H_5$ | N | N | C—$NHCH_3$ |
| $CH_3$ | $CH_3$ | CH | CH | C—$CH_3$ |

The starting substances of the formula (III) are not yet known from the literature.

The new N-heteroaryl-iminodithiocarbonic acid S,S-diesters of the general formula (III) are obtained by a process in which aminohetarenes of the general formula (IV)

in which
$R^3$, X, Y and Z have the abovementioned meanings,
—or metal salts of compounds of the formula (IV)—are reacted with carbon disulphide in the presence of a strong base, such as, for example, sodium hydroxide or potassium hydroxide, and in the presence of a diluent, such as, for example, dimethylformamide and/or water, at temperatures between −20° C. and +50° C., and the products are further reacted in situ with alkylating agents of the general formula (V)

in which
$R^2$ has the abovementioned meaning and
$X^1$ represents chlorine, bromine or iodine, at temperatures between 0° C. and 100° C. The products of the formula (III) obtained as crystals after dilution with water can be isolated by filtration with suction.

Formula (IV) provides a general definition of the aminohetarenes to be used as intermediate products. In formula (IV), $R^3$, X, Y and Z preferably or in particular have those meanings which have already been mentioned above as preferred or as particularly preferred for $R^3$, X, Y and Z in connection with the description of the compounds of the formula (III) according to the invention.

Examples which may be mentioned of the compounds of the formula (IV) are: 2-amino-4,6-dimethyl-pyrimidine, -4-methyl-6-methoxy-pyrimidine, -4,6-dimethoxy-pyrimidine, -4-methyl-6-ethoxy-pyrimidine, -4-chloro-6-methoxy-pyrimidine, -4-methyl-pyrimidine, -4-chloro-6-methyl-pyrimidine, -4-trifluoromethyl-6-methoxy-pyrimidine, -4-methoxy-6-difluoromethoxy-pyrimidine, -4-methyl-6-difluoromethoxy-pyrimidine, -4,6-bis-difluoro-methoxy-pyrimidine, -4-chloro-6-ethoxy-pyrimidine, -4,6-diethoxy-pyrimidine, -4,5-dichloro-6-methyl-pyrimidine, -4-methyl-5-chloro-6-methoxy-pyrimidine, -4,6-dichloro-pyrimidine, -4-ethyl-6-methoxy-pyrimidine, -5-chloro-4,6-dimethoxy-pyrimidine and -4,6-bis-trifluoromethyl-pyrimidine, and furthermore 2-amino-4,6-dimethyl-s-triazine, -4-methyl-6-methoxy-striazine, -4,6-dimethoxy-s-triazine, -4-ethyl-6-methoxy-s-triazine and -4-methyl-6-ethoxy-s-triazine.

The aminohetarenes of the formula (IV) are known and/or can be prepared by processes which are known per se (compare Chem. Pharm. Bull. 11 (1963), 1382; U.S. Pat. No. 4,299,960; EP-A Nos. 121,082; 125,205; 126,711; 152,378 and 158,594).

Formula (V) provides a general definition of the alkylating agents furthermore required as intermediate products. In formula (V), $R^2$ preferably or in particular has that meaning which has already been mentioned above as preferred or as particularly preferred for $R^2$ in connection with the description of the compounds of the formula (III) according to the invention, and $X^1$ also preferably represents chlorine, bromine or iodine.

Examples which may be mentioned of the alkylating agents of the formula (V) are: methyl and ethyl chloride, bromide and iodide, chloro- and bromo-acetic acid and the methyl and ethyl esters thereof and benzyl chloride and bromide.

The compounds of the formula (V) are known organic synthesis chemicals.

The process according to the invention for the preparation of the sulphonylisothioureas of the formula (I) is preferably carried out using diluents. Possible diluents here are virtually all the customary organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, alcohols, such as methanol, ethanol, propanol, isopropanol, butanol, isobutanol, sec.-butanol, tert.-butanol, pentanol, isopentanol, sec.-pentanol and tert.-pentanol, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and dimethyl sulphoxide, tetramethylene sulphone and hexamethylphosphoric acid triamide.

Acid acceptors which can be used in the process according to the invention are all the acid-binding agents which can usually be employed for such reactions. Preferred possible acid-binding agents are alkali metal hydroxides, such as, for example, sodium hydroxide and potassium hydroxide, alkaline earth metal hydroxides, such as, for example, calcium hydroxide, alkali metal carbonates and alcoholates, such as the methylate, ethylate, propylate, isopropylate, butylate, isobutylate, sec.-butylate and tert.-butylate of sodium and potassium, and sodium hydride, potassium hydride and calcium hydride.

The process according to the invention is in general carried out at temperatures between 20° C. and 200° C., preferably between 60° C. and 140° C., and in general under normal pressure.

For carrying out the process according to the invention, the starting substances can be employed in various molar ratios. An excess of one or the other of the components, however, does not provide substantial advantages. The starting substances are therefore preferably employed in approximately equimolar amounts.

The starting substances can be brought together in any desired sequence. In a preferred embodiment of the process according to the invention, a metal salt of the compound of the formula (II) is first produced from a sulphonic acid amide of the formula (II) and one of the abovementioned acid acceptors, preferably in the presence of one of the abovementioned diluents. An N-heteroaryliminodithiocarbonic acid S,S-diester of the formula (III) is then added to this product and the reaction mixture is stirred at the particular required temperature until the reaction has ended.

Working up can be carried out by customary methods. In general, after cooling to temperatures of between 0° C. and 20° C., the mixture is acidified with an aqueous proton acid, such as, for example, hydrochloric acid or sulphuric acid, and extracted with an organic solvent which is practically immiscible with water, such as, for example, methylene chloride. The organic phase is concentrated and the product of the formula (I) remaining in the residue is crystallized, for example by trituration with alcohol, and isolated by filtration with suction.

The sulphonylisothioureas of the formula (I) to be prepared by the process according to the invention can be used as herbicides (compare EP-A No. 5,986).

PREPARATION EXAMPLES

EXAMPLE 1

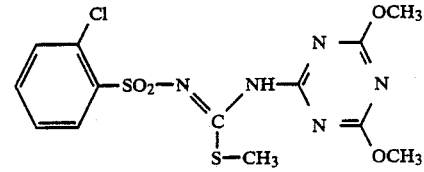

13.0 g (0.05 mol) of S,S-dimethyl N-(4,6-dimethoxy-s-triazin-2-yl)-iminodithiocarbonate are added to a suspension of the sodium salt of 2-chloro-benzenesulphonamide (0.05 mol) in 80 ml of dioxane at 20° C. and the reaction mixture is stirred at 90° C. to 100° C. for 15 hours. After cooling to 20° C., it is acidified with 2N hydrochloric acid and extracted with methylene chloride. The methylene chloride solution is concentrated, the residue is triturated with ethanol and the product obtained in this way as crystals is isolated by filtration with suction.

3.6 g (68% of theory) of N'-(4,6-dimethoxy-s-triazin-2-yl)-N''-(2-chloro-phenylsulphonyl)-S-methyl-isothiourea of melting point 159° C. are obtained.

Starting substances of the formula (III)

EXAMPLE (III-1)

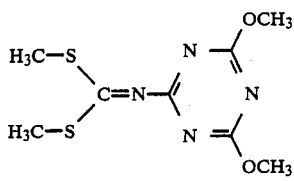

12.5 g (0.22 mol) of potassium hydroxide powder are added in portions to a mixture of 15.4 g (0.10 mol) of 2-amino-4,6-dimethoxy-s-triazine, 8.5 g (0.11 mol) of carbon disulphide and 80 ml of dimethylformamide, during which the internal temperature is kept below 35° C. The reaction mixture is then stirred at 45° C. for 30 minutes. 31 g (0.22 mol) of methyl iodide are subsequently added dropwise, with further stirring, and stirring is continued at 40° C. for a further 60 minutes. After cooling, the mixture is diluted with 250 ml of water and the product obtained in this way as crystals is isolated by filtration with suction.

23.6 g (90% of theory) of S,S-dimethyl N-(4,6-dimethoxy-s-triazin-2-yl)-iminodithiocarbonate of melting point 123° C. are obtained.

EXAMPLE (III-2)

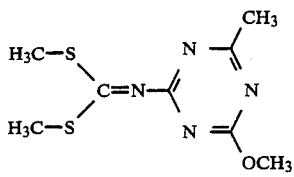

S,S-dimethyl N-(4-methoxy-6-methyl-s-triazin-2-yl)-iminodithiocarbonate, of the above formula, is obtained analogously to Example (III-1) in equally high yield. Melting point: 78° C.

It will be appreciated that the instant specification and claims are set forth by way of illustration and not limitation, and that various modifications and changes may be made without departing from the spirit and scope of the present invention.

I claim:

1. A process for the preparation of a sulphonylisothiourea of the formula

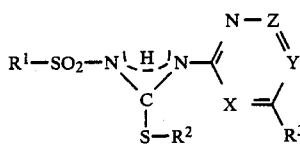

in which
R$^1$ represents an optionally substituted radical from the group consisting of alkyl, aralkyl, aryl and heteroaryl,
R$^2$ represents in each case optionally substituted alkyl or aralkyl,
R$^3$ represents hydrogen, halogen, hydroxyl, amino or an optionally substituted radical from the group consisting of alkyl, alkoxy, alkylthio, alkylamino and dialkylamino,
X represents nitrogen or a CH grouping,
Y represents nitrogen or a CR$^4$ grouping, wherein
R$^4$ represents hydrogen, halogen, cyano, alkyl, formyl, alkylcarbonyl or alkoxycarbonyl, and
Z represents nitrogen or a CR$^5$ grouping, wherein
R$^5$ represents hydrogen, halogen, hydroxyl, amino or an optionally substituted radical from the group consisting of alkyl, alkoxy, alkylthio, alkylamino and dialkylamino,
which comprises reacting a sulphonic acid amide of the formula $$R^1-SO_2-NH_2, \quad (II)$$

or a metal salt thereof, with an N-heteroaryl-iminodithiocarbonic acid S,S-diester of the formula

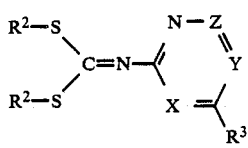

at a temperature between about 20° C. and 200° C.

2. The process according to claim 1, wherein the temperature is between about 60° C. and 140° C.

3. The process according to claim 1, in which
R$^1$ represents the radical

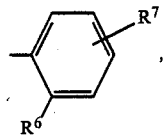

wherein
R$^6$ represents hydrogen, halogen, cyano, nitro, C$_1$-C$_4$-alkyl (which is optionally substituted by halogen, cyano, C$_1$-C$_4$-alkoxy or C$_1$-C$_4$-alkoxycarbonyl), C$_1$-C$_4$-alkoxy (which is optionally substituted by halogen, cyano, C$_1$-C$_4$-alkoxy or C$_1$-C$_4$-alkoxy-carbonyl) or C$_1$-C$_4$-alkylthio, C$_1$-C$_4$-alkylsulphinyl or C$_1$-C$_4$-alkylsulphonyl (which are optionally substituted by halogen, cyano, C$_1$-C$_4$-alkoxy or C$_1$-C$_4$-alkoxy-carbonyl), or di-(C$_1$-C$_4$-aminosulphonyl, N represents (C$_1$-C$_4$-alkoxy)-N-C$_1$-C$_4$-alkyl-aminosulphonyl, phenyl, phenoxy, C$_1$-C$_4$-alkoxy-carbonyl or di-(C$_1$-C$_4$-alkylamino)-carbonyl and
R$^7$ represents hydrogen or halogen,
or
R$^1$ represents the radical

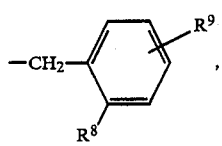

wherein
R$^8$ represents hydrogen, halogen, cyano, nitro, C$_1$-C$_4$-alkyl (which is optionally substituted by halogen, cyano, C$_1$-C$_4$-alkoxy or C$_1$-C$_4$-alkoxycarbonyl), $C_1$–$C_4$-alkoxy (which is optionally substituted by halogen, cyano, $C_1$–$C_4$-alkoxy or $C_1$–$C_4$-alkoxy-carbonyl) or $C_1$–$C_4$-alkylthio, $C_1$–$C_4$-alkylsulphinyl or $C_1$–$C_4$-alkylsulphonyl (which are optionally substituted by halogen, cyano, $C_1$–$C_4$-alkoxy or $C_1$–$C_4$-alkoxy-carbonyl), or represents di-($C_1$–$C_4$-alkyl)-aminosulphonyl or $C_1$–$C_4$-alkoxy-carbonyl and $R^9$ represents hydrogen or halogen, or $R^1$ represents the radical

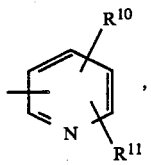

wherein $R^{10}$ represents hydrogen, halogen, cyano, nitro, $C_1$–$C_4$-alkyl (which is optionally substituted by halogen), $C_2$–$C_4$-alkenyl (which is optionally substituted by halogen), $C_1$–$C_4$-alkoxy (which is optionally substituted by halogen), $C_1$–$C_4$-alkylthio, $C_1$–$C_4$-alkylsulphinyl or $C_1$–$C_4$-alkylsulphonyl (which are optionally substituted by halogen), di-($C_1$–$C_4$-alkyl)-aminosulphonyl, $C_1$–$C_4$-alkoxycarbonyl, di-($C_1$–$C_4$-alkyl)-aminocarbonyl or dioxolanyl and $R^{11}$ represents hydrogen or halogen, or $R^1$ represents the radical

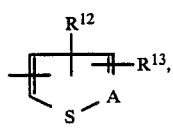

wherein

A represents nitrogen or a CH grouping, $R^{12}$ represents hydrogen, halogen, cyano, nitro, $C_1$–$C_4$-alkyl (which is optionally substituted by halogen, $C_1$–$C_4$-alkoxy or $C_1$–$C_4$-halogenoalkoxy), $C_1$–$C_4$-alkoxy (which is optionally substituted by halogen or $C_1$–$C_4$-alkoxy, $C_1$–$C_4$-alkylthio, $C_1$–$C_4$-alkylsulphinyl or $C_1$–$C_4$-alkylsulphonyl (which are optionally substituted by halogen), di-($C_1$–$C_4$-alkyl)-aminosulphonyl or $C_1$–$C_4$-alkoxycarbonyl and $R^{13}$ represents hydrogen or halogen, or $R^1$ represents the radical

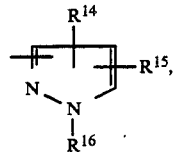

wherein $R^{14}$ represents hydrogen, halogen, cyano, nitro, $C_1$–$C_4$-alkyl (which is optionally substituted by halogen), $C_1$–$C_4$-alkoxy (which is optionally alkoxy-carbonyl, $R^{15}$ represents hydrogen or halogen and $R^{16}$ represents hydrogen, $C_1$–$C_4$-alkyl, phenyl or (iso)quinolinyl, or $R^1$ represents the radical

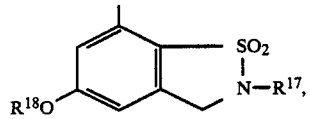

wherein $R^{17}$ and $R^{18}$ represent $C_1$–$C_4$-alkyl, or $R^1$ represents the radical

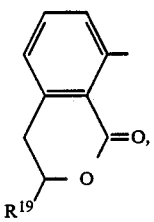

wherein $R^{19}$ represents hydrogen or methyl.

4. The process according to claim 1, in which $R^1$ represents the radical

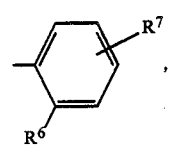

wherein $R^6$ represents fluorine, chlorine, bromine, methyl, trifluoromethyl, methoxy, difluoromethoxy, trifluoromethoxy, methylthio, methylsulphonyl, dimethylaminosulphonyl, N-methoxy-N-methylaminosulphonyl, phenyl, methoxycarbonyl or ethoxycarbonyl and $R^7$ represents hydrogen, fluorine or chlorine.

5. The process according to claim 1, in which $R^2$ represents $C_1$–$C_6$-alkyl (which is optionally substituted by fluorine, chlorine, cyano, $C_1$–$C_2$-alkoxy, carboxyl, $C_1$–$C_2$-alkoxy-carbonyl, aminocarbonyl, $C_1$–$C_2$-alkylaminocarbonyl or di-($C_1$–$C_2$-alkyl)-amino-carbonyl, or represents benzyl or phenethyl (which are optionally substituted in the phenyl part by fluorine, chlorine, $C_1$–$C_2$-alkyl, $C_1$–$C_2$-halogenoalkyl, $C_1$–$C_2$-alkoxy, $C_1$–$C_2$-halogenoalkoxy or $C_1$–$C_2$-alkoxycarbonyl), $R^3$ represents hydrogen, fluorine, chlorine, bromine, $C_1$–$C_4$-alkyl, $C_1$–$C_4$-halogenoalkyl, $C_1$–$C_4$-alkoxy-$C_1$–$C_2$-alkyl, $C_1$–$C_4$-alkoxy, $C_1$–$C_4$-halogenoalkoxy, $C_1$–$C_4$-alkylthio, $C_1$–$C_4$-halogenoalkylthio, amino, $C_1$–$C_4$-alkylamino, dimethylamino or diethylamino, X represents nitrogen or a CH grouping, Y represents nitrogen or a $CR^4$ grouping, wherein $R^4$ represents hydrogen, fluorine, chlorine, bromine, cyano, methyl, formyl, acetyl, methoxycarbonyl or ethoxycarbonyl and Z represents nitrogen or a $CR^5$ grouping, wherein
$R^5$ represents hydrogen, fluorine, chlorine, bromine, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-alkylamino, dimethylamino or diethylamino.

6. The process according to claim 1, in which
$R^2$ represents methyl, ethyl, carboxymethyl, methoxycarbonylmethyl, ethoxycarbonylmethyl or benzyl,
$R^3$ represents hydrogen, fluorine, chlorine, bromine, methyl, ethyl, trifluoromethyl, methoxy, ethoxy, difluoromethoxy, methylthio, ethylthio, amino, methylamino, ethylamino, dimethylamino or diethylamino, X represents nitrogen or a CH grouping, Y represents nitrogen or a $CR^4$ grouping, wherein
$R^4$ represents hydrogen, fluorine, chlorine or methyl, and Z represents nitrogen or a $CR^5$ grouping, wherein
$R^5$ represents hydrogen, fluorine, chlorine, bromine, methyl, ethyl, trifluoromethyl, methoxy, ethoxy, propoxy, isopropoxy, difluoromethoxy, methylthio, ethylthio, methylamino, ethylamino, dimethylamino or diethylamino.

* * * * *

UNITED STATES PATENT AND TRADEMARK OFFICE
CERTIFICATE OF CORRECTION

PATENT NO. : 4,968,796

DATED : November 6, 1990

INVENTOR(S) : Hans-Jochem Riebel

It is certified that error appears in the above-identified patent and that said Letters Patent is hereby corrected as shown below:

Col. 10, line 50     After " or " delete " di-($C_1$-$C_4$-aminosulphonyl, N represents " and substitute -- represents di-($C_1$-$C_4$-alkyl)-aminosulphonyl, N- --

Col. 11, line 6     After 1st " $C_1$ " delete " a " and substitute -- - --

Col. 12, line 1     After " optionally " insert -- substituted by halogen), dioxolanyl or $C_1$-$C_4$- --

Col. 12, line 55     After second " $C_2$ " delete " C "

Signed and Sealed this

Twentieth Day of October, 1992

*Attest:*

DOUGLAS B. COMER

*Attesting Officer*     *Acting Commissioner of Patents and Trademarks*